US00PP30660P3

(12) United States Plant Patent
Helmuth

(10) Patent No.: US PP30,660 P3
(45) Date of Patent: Jul. 9, 2019

(54) APPLE TREE NAMED 'DUKE FUJI'

(50) Latin Name: ***Malus domestica* Borkh.**
Varietal Denomination: Duke Fuji

(71) Applicant: KIKU SRL GmbH, Girlan/Eppan (IT)

(72) Inventor: Danay Helmuth, Andrian (IT)

(73) Assignee: KIKU SRL GmbH, Girlan/Eppan (IT)

( * ) Notice: Subject to any disclaimer, the term of this patent is extended or adjusted under 35 U.S.C. 154(b) by 1 day.

(21) Appl. No.: 15/732,102

(22) Filed: Sep. 18, 2017

(65) Prior Publication Data

US 2018/0139877 P1 May 17, 2018

(30) Foreign Application Priority Data

Nov. 11, 2016 (IT) ..... 122016000113925

(51) Int. Cl.
*A01H 5/08* (2018.01)
*A01H 6/74* (2018.01)

(52) U.S. Cl.
USPC ..... Plt./168
CPC ..... *A01H 6/7418* (2018.05); *A01H 5/08* (2013.01)

(58) Field of Classification Search
USPC ..... Plt./168
CPC ..... A01H 5/0875
See application file for complete search history.

*Primary Examiner* — Kent L Bell
(74) *Attorney, Agent, or Firm* — Michelle Bos Legal LLC

(57) ABSTRACT

'Duke Fuji' apple tree is a naturally occurring limb sport mutation of 'Brak' Fuji notable for its distinctive fruit, which has an attractive sold red flush. 'Duke Fuji' colors early and evenly, allowing it to be harvested in a single picking.

7 Drawing Sheets

Latin name: *Malus domestica* Borkh.
Variety denomination: 'Duke Fuji'.

BACKGROUND OF THE VARIETY

'Duke Fuji' is a new and distinct variety of apple tree (*Malus domestica* Borkh), which originated as a naturally occurring limb sport mutation of 'Brak' Fuji (U.S. Plant Pat. No. 15,261). 'Duke Fuji' was discovered by the inventor in a cultivated orchard at Andrian, Italy in 2009, and was selected for further observation because of the distinctive early and even coloring of its fruit. 'Duke Fuji' was first asexually propagated by chip budding in 2010 at Presina, Italy, and has since been observed to remain true to type over successive asexually propagated generations.

BRIEF DESCRIPTION OF THE VARIETY

'Duke Fuji' was first selected for its distinctive fruit, which is fully and evenly colored well before harvest. Fruit of 'Duke Fuji' is also distinguished by its attractive deep red color and its readiness for harvest in a single pick.

'Duke Fuji' is distinguished from parent 'Brak' by its fruit, which exhibits a solid flush overcolor as compared to the striped overcolor of 'Brak'. Fruit of 'Duke Fuji' colors earlier than 'Brak' and can be picked in a single picking, as compared with two pickings required for 'Brak'.

'Duke Fuji' is also distinguished from similar variety 'Fubrax' (U.S. Plant Pat. No. 18,761) by intense red solid flush overcolor of its fruit, as compared to the striped overcolor of 'Fubrax'. Young fruit of 'Duke Fuji' exhibits much greater anthocyanin coloration than young fruit of 'Fubrax'.

'Duke Fuji' is distinguished from similar variety 'Aztec' by its fruit. 'Aztec' colors later and less evenly than 'Duke Fuji', and exhibits a medium to dark red striping pattern over a yellow green ground as compared to the intense red solid flush overcolor of 'Duke Fuji'. 'Aztec' requires more than one picking, as compared to the single picking required for 'Duke Fuji'. The stem of 'Aztec' fruit is light brown in color as compared to the darker brown stem of 'Duke Fuji'.

BRIEF DESCRIPTION OF THE PHOTOGRAPHS

Figure 1:
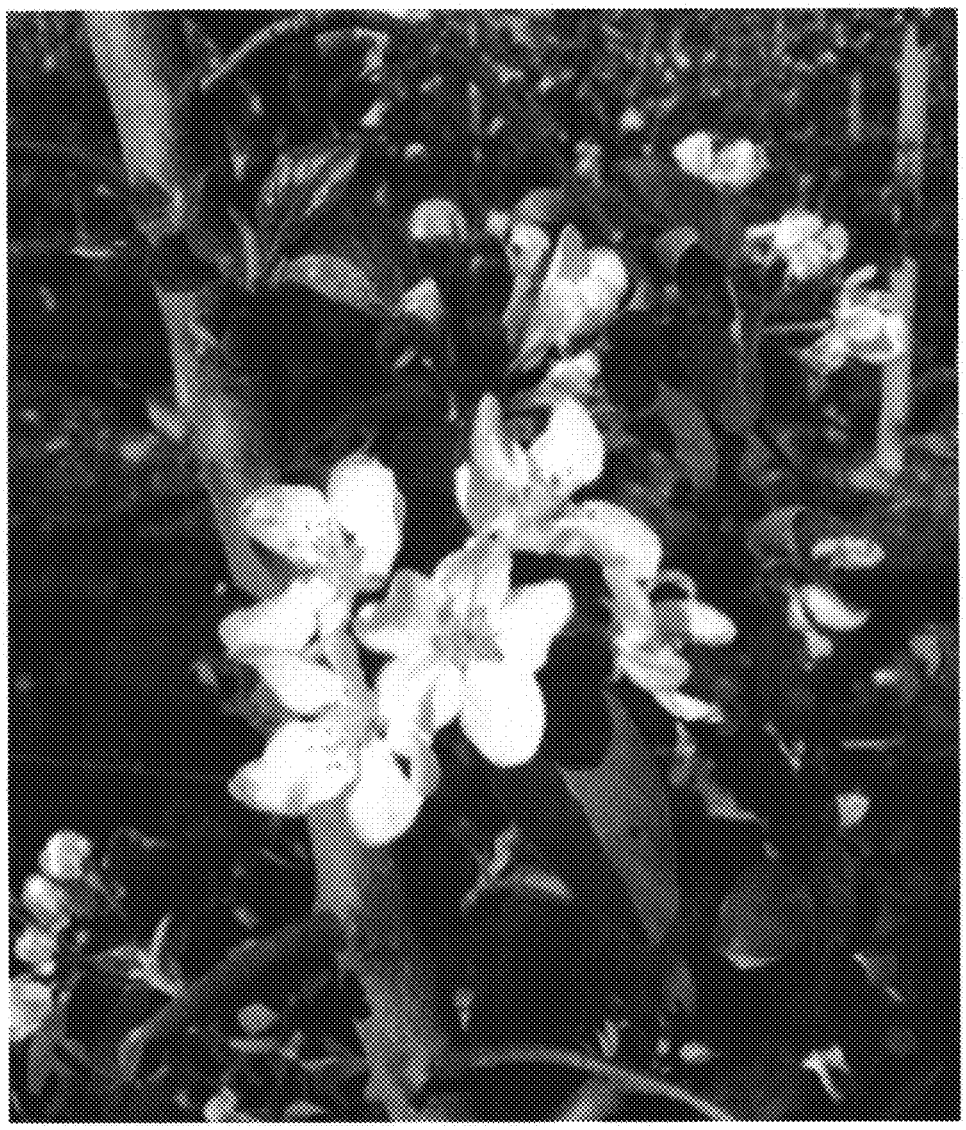
FIG. 1 shows blossoms, trunk and leaves of a 'Duke Fuji' tree.
Figure 2:
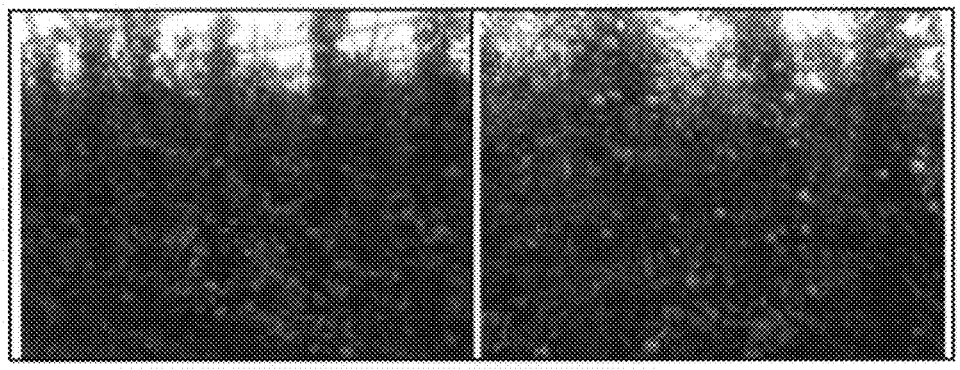
FIG. 2 shows a comparison of fruit color on 'Duke Fuji' and 'Aztec' trees.
Figure 3:
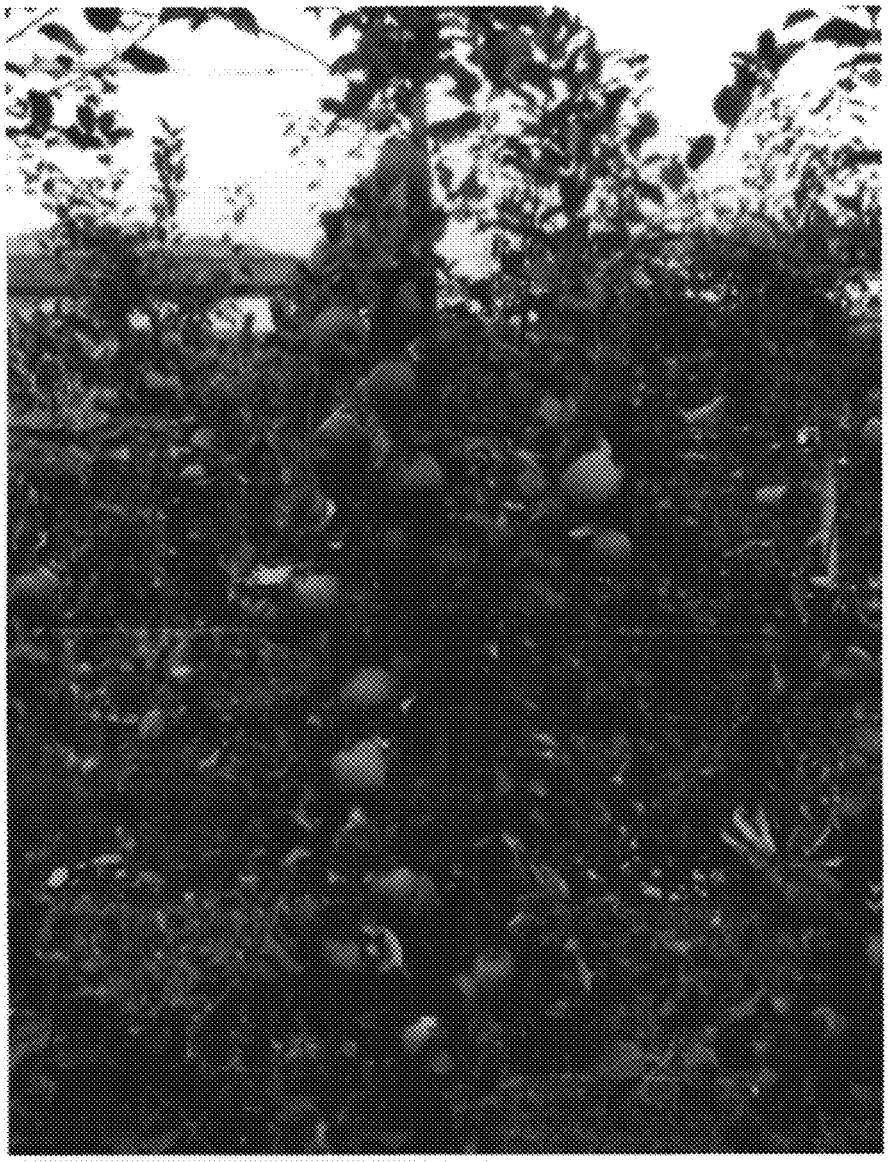
FIG. 3 shows a 'Duke Fuji' tree and fruit.
Figure 4:
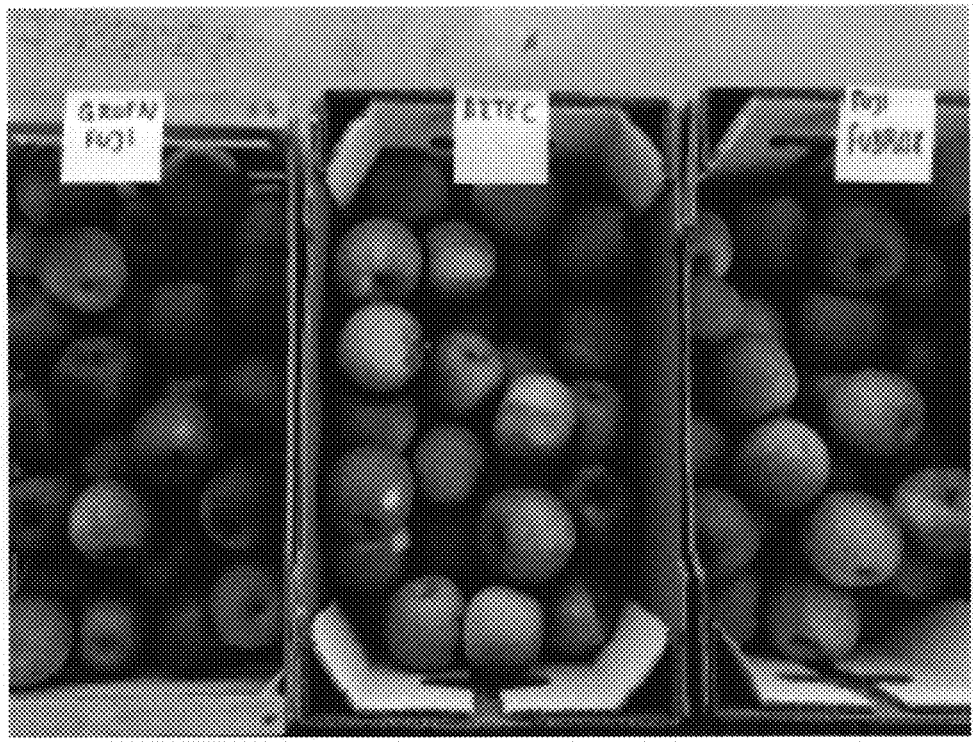
FIG. 4 shows fruit of 'Duke Fuji' (left), 'Aztec' (center) and 'Fubrax' (right)
Figure 5:
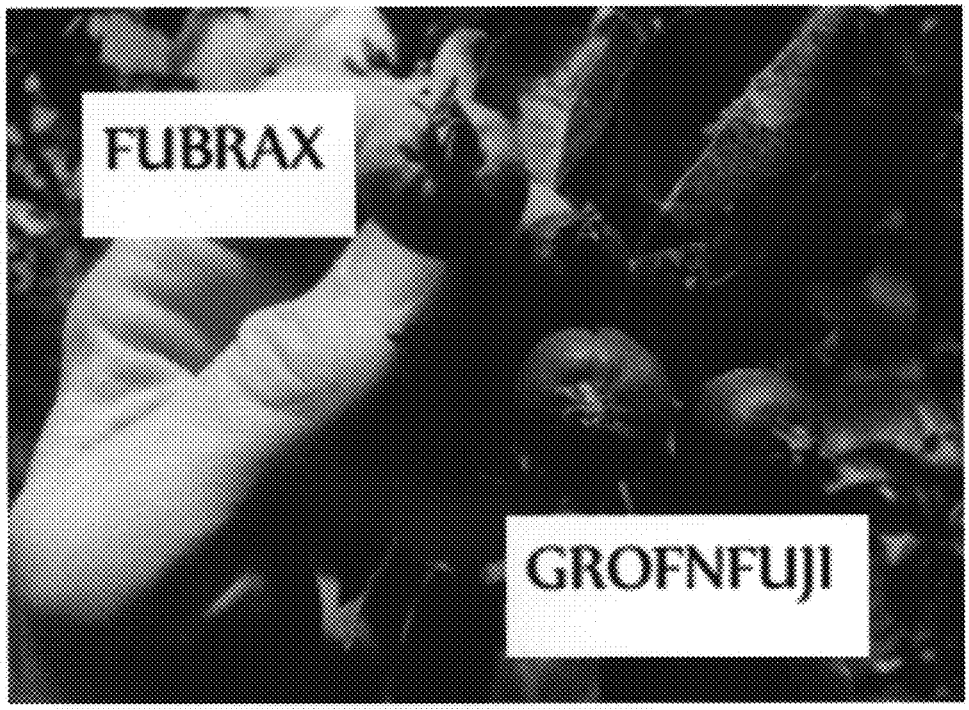
FIG. 5 shows young fruit of 'Fubrax' (left) and 'Duke Fuji' (right)
Figure 6:
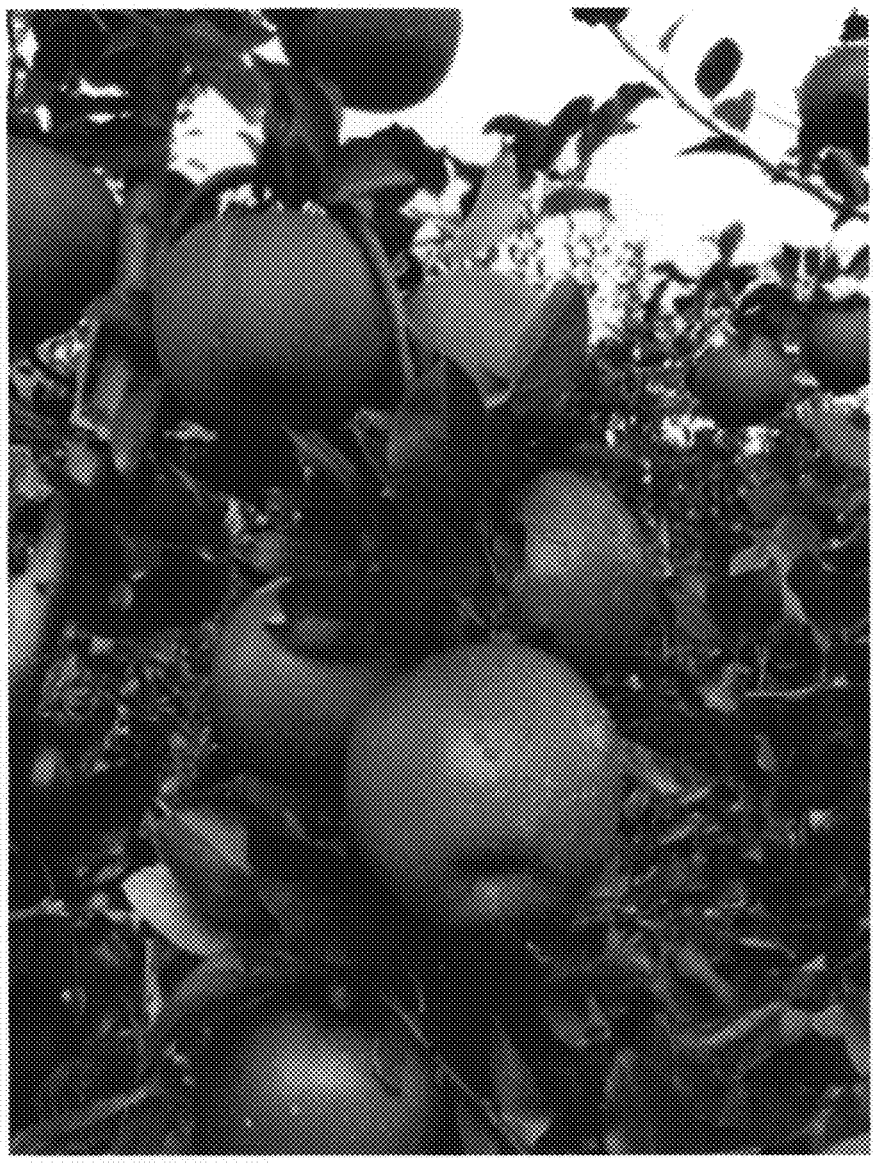
FIG. 6 shows fruit and leaves of 'Duke Fuji'.
Figure 7:
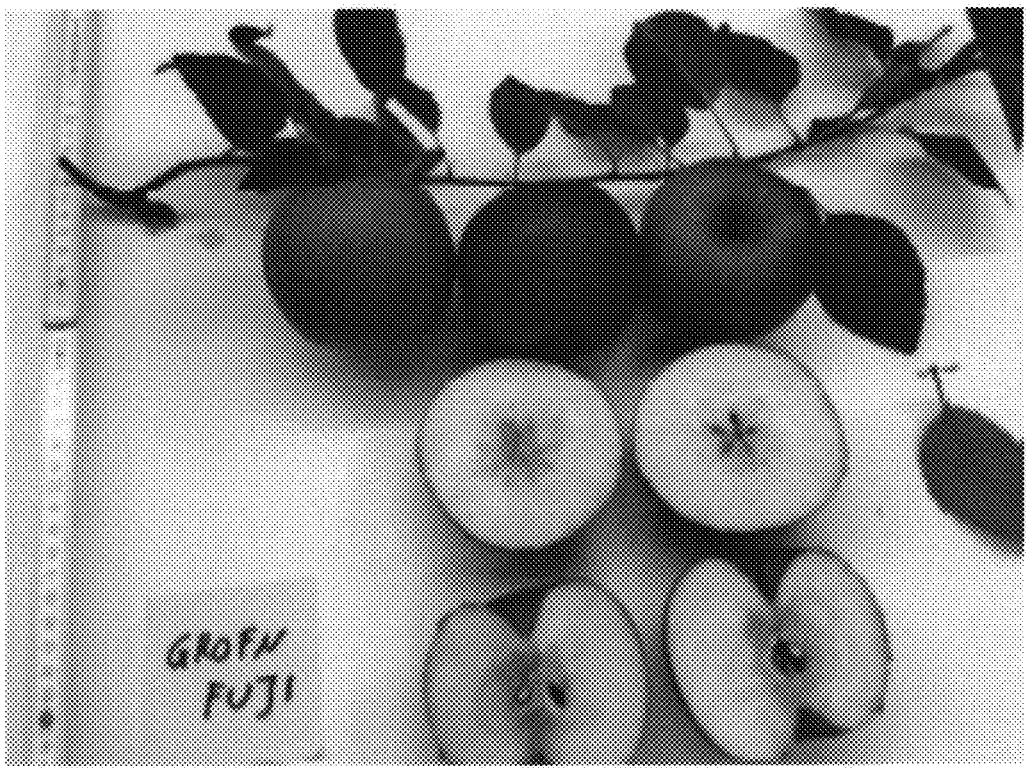
FIG. 7 shows leaves and whole and sectioned fruit of 'Duke Fuji'.

Actual colors will vary with lighting conditions; color characteristics of 'Duke Fuji' apple tree should therefore be determined with reference to the observations described herein below, rather than from these illustrations alone.

DETAILED BOTANICAL DESCRIPTION OF THE VARIETY

The attached illustrations and the following detailed botanical description of 'Duke Fuji' apple tree are based on observations made and photographs taken during the 2014 through 2017 growing seasons at Cornaiano, Italy of trees planted in 2012 on M9 T337 virus free rootstock. All colors are described according to The Royal Horticultural Society Colour Chart. The characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor.*—Strong, typical of 'Fuji' varieties.
- *Type.*—Ramified.
- *Habit.*—Drooping.
- *Height.*—1.7 m to 1.8 m (1 year old tree). 2.2 to 2.5 m (2 year old tree).
- *Trunk diameter at 30 cm above the graft.*—12 mm to 16 mm (1 year old tree). 25 to 30 mm (2 year old tree).
- *Bark texture.*—Smooth.
- *Bark color.*—Greyed-green 197A.
- *Type of bearing.*—On spurs and long shoots.

Branch (fruiting branches located at around 1 m above the graft union):
- *Length.*—50 cm to 100 cm.
- *Diameter.*—1.5 cm+/−0.1 cm at 5 cm from the stem.
- *Crotch angle.*—35 to 45 degrees (1 and 2 year old tree) 55 to 60 degrees (3 year old tree).
- *Bark color.*—Brown N200B; Brown N200C on older trees.
- *Lenticel length.*—0.19 cm+/−0.03 cm.
- *Lenticel color.*—White 155A to 155B.
- *Number of lenticels.*—8+/−4 per $cm^2$.

One year old shoot:
- *Length.*—30 cm to 50 cm (1 year old tree) 50 to 60 cm (2 year old tree).
- *Color.*—Greyed-orange 177A.
- *Pubescence.*—Weak.
- *Thickness.*—0.8 cm+/−0.1 cm (medium).
- *Internode length.*—Medium, about 3 cm.
- *Number of lenticels.*—Many, 8+/−6 per $cm^2$.

Flower buds:
- *Quantity per spur.*—6.
- *Shape.*—Oval.
- *Length.*—0.6 cm.
- *Diameter.*—0.4 cm.
- *Color.*—Greyed-purple N187A.

Flowers: Diameter of fully open flower 4 cm+/−0.5 cm.
- *Relative position of petal margin.*—Touching.
- *Number per cluster.*—5 plus king flower.
- *Date of first bloom.*—April 8 (typical of 'Fuji').
- *Date of full bloom.*—April 17.
- *Pollination requirement.*—Pollenizer such as 'Gala' required.
- *Color at balloon stage.*—Red 52A.

Petals (measured on king flower):
- *Number per flower.*—5.
- *Shape.*—Oval.
- *Length.*—2.4 cm+/−0.2 cm.
- *Width.*—1.4 cm+/−0.2 cm.
- *Apex.*—Round.
- *Base.*—Pointy.
- *Margin.*—Unruffled.
- *Color of upper surface.*—White N155D.
- *Color of lower surface.*—White N155D with slight traces of red 47A on edges.

Pistils:
- *Size.*—Vessels of pistil are erect, number from 10 to 12, length 5.5 mm.
- *Color.*—Green 138B.

Stigma:
- *Position.*—Above anthers (like 'Golden Delicious').
- *Size.*—0.08 cm+/−0.1 cm.
- *Color.*—Yellow 5A.

Style:
- *Size.*—1.0 cm+/−0.2 cm.
- *Color.*—Yellow-green 145C.

Ovary:
- *Length.*—0.5 cm+/−0.1 cm.
- *Color.*—Yellow-green 144A.

Anthers:
- *Quantity.*—10+/−2.
- *Length.*—0.6 cm+/−0.1 cm.
- *Presence of pollen.*—Present, abundant.
- *Pollen color.*—Yellow-orange 17A.
- *Anther color.*—Yellow-orange 17A.

Stamen:
- *Length.*—5.5 mm.
- *Color.*—Green 138B.

Pedicel:
- *Length.*—3 cm+/−0.8 cm.
- *Diameter.*—0.16 cm+/−0.02 cm.
- *Color.*—Yellow-green 145A.
- *Texture.*—Pubescent.

Sepals:
- *Quantity.*—5.
- *Color.*—Yellow-green 145A.
- *Shape.*—Pointed, triangular.
- *Margin.*—Smooth.
- *Length.*—0.75 cm+/−0.05 cm.
- *Width.*—0.5 cm+/−0.05 cm.
- *Texture.*—Upper surface smooth, lower surface pubescent.

Leaves:
- *Shape.*—Elliptic.
- *Length.*—Up to about 10 cm.
- *Width.*—Up to about 6 cm.
- *Length/width ratio.*—2+/−0.1 to 1.
- *Blade margin.*—Serrulate.
- *Apex.*—Acute.
- *Base shape.*—Aequilateral.
- *Color of upper surface.*—Green 137A to 137B for younger trees Green 138A for older trees.
- *Color of lower surface.*—Green 137C to 138A for younger trees Green 137C for older trees.
- *Texture of upper surface.*—Smooth.
- *Texture of lower surface.*—Pubescent.
- *Vein color.*—Upper surface — Yellow-green 145B.
- *Vein color.*—Lower surface — Red 47B.
- *Attitude in relation to shoot.*—Outward.

Petiole:
- *Length.*—2.6 cm to 3.6 cm.
- *Diameter.*—1.2 cm+/−0.1 cm.
- *Color.*—Green 138B.

Fruit:
- *Quantity per cluster.*—Up to 5.
- *Diameter.*—88 mm+/−8 mm.
- *Height.*—88 mm+/−8 mm.
- *Weight.*—270 g+/−25 g.
- *Ratio of height to width.*—1 to 1.
- *General shape in profile.*—Globose.
- *Position of maximum diameter.*—50% in profile.
- *Ribbing.*—Absent or weak.
- *Crowning at calyx end.*—Absent or weak.

*Depth of eye basin*.—Small: 1 cm deep.
*Width of eye basin*.—2.8 cm+/−0.2 cm.
*Bloom of skin*.—Medium.
*Greasiness of skin*.—Absent.
*Skin texture*.—Smooth with prominent lenticels.
*Background color of skin*.—Not visible.
*Amount of over color*.—100%.
*Over color of skin*.—Red 46A.
*Intensity of over color*.—High.
*Pattern of over color*.—Only solid flush.
*Amount of russet around stalk cavity*.—Absent or small.
*Amount of russet on cheeks*.—Absent.
*Area of russet around eye basin*.—Absent.
*Length of stalk*.—Short, 1.7 cm+/−0.3 cm.
*Thickness of stalk*.—Medium, 1.8 cm 30 /−0.2 cm.
*Stalk texture*.—Smooth.
*Stalk color*.—Greyed-orange 177A.
*Depth of stalk cavity*.—Medium, 1.2 cm+/−0.1 cm.
*Width of stalk cavity*.—Broad, 2.8 cm+/−0.1 cm.
*Firmness of flesh*.—Medium, 6.5 kg per $cm^2$.
*Flesh texture*.—Crunchy.
*Aroma*.—Sweet.
*Juiciness*.—High.
*Brix*.—14 to 15.
*Flesh color*.—Yellow 13D.
*Number of lenticels*.—5 to 8 per $cm^2$.
*Lenticel diameter*.—Medium, up to 1.5 mm.
*Color of lenticels*.—Greyed-yellow 160B.
*Locules*.—5 per fruit; width 0.4 cm+/−0.1 cm.
*Aperture of locules*.—Moderately open.

Seeds:
*Quantity per fruit*.—Up to 2 per chamber, up to 10 per fruit.
*Shape*.—Pointed.
*Length*.—0.8 cm+/−0.1 cm.
*Width*.—0.5 cm+/−0.1 cm.
*Color*.—Greyed-orange 166C.

Harvest:
*Time for harvest*.—Mid-October, similar to other mid-season 'Fuji'-type varieties.
*Number of picks*.—1.
*Amount of fruit produced per tree per harvest*.—25 kg+/−2 kg.
*Disease resistance/susceptibility*.—None noted; same as other 'Fuji'-type. varieties
*Market use*.—Fresh.
*Storageability*.—Up to 7 months in controlled atmosphere storage.

I claim:

1. A new and distinct Apple tree, substantially as described and illustrated herein.

* * * * *

GROFNFUJI AZTEC